United States Patent
Brooks

(10) Patent No.: US 9,492,513 B2
(45) Date of Patent: Nov. 15, 2016

(54) METHODS FOR TREATMENT OF HIP AND GROIN PAIN ASSOCIATED WITH FEMOROACETABULAR IMPINGEMENT (FAI)

(71) Applicant: Allergan, Inc., Irvine, CA (US)

(72) Inventor: Gregory F. Brooks, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 356 days.

(21) Appl. No.: 14/259,870

(22) Filed: Apr. 23, 2014

(65) Prior Publication Data
US 2014/0322197 A1 Oct. 30, 2014

Related U.S. Application Data

(60) Provisional application No. 61/815,902, filed on Apr. 25, 2013.

(51) Int. Cl.
*A61K 38/48* (2006.01)
*A61K 45/06* (2006.01)

(52) U.S. Cl.
CPC ........... *A61K 38/4893* (2013.01); *A61K 45/06* (2013.01)

(58) Field of Classification Search
None
See application file for complete search history.

(56) References Cited

U.S. PATENT DOCUMENTS

2007/0020294 A1* 1/2007 Marchini ........... A61K 38/4893
424/239.1
2009/0232850 A1* 9/2009 Manack ............... A61K 38/164
424/239.1

OTHER PUBLICATIONS

Lundy et al. "Botulinum toxin type A injections can be an effective treatment for pain in children with hip spasms and cerebral palsy" Developmental Medicine & Child Neurology 2009, 51: 705-710.*
Marchini et al. "Efficacy of Botulinum Toxin Type A Treatment of Functional Impairment of Degenerative Hip Joint: Preliminary Results" J Rehabil Med 2010; 42: 691-693.*
Willoughby et al. "The impact of botulinum toxin A and abduction bracing on long-term hip development in children with cerebral palsy" Developmental Medicine & Child Neurology 2012, 54: 743-747.*
Benjamin R. Kivlan, Response to Diagnostic Injection in Patients with Femoroacetabular Impingement, Labral Tears, Chondral Lesions, and Extra-Articular Pathology, Arthroscopy The Journal of Arthroscopic and Related Surgery, May 2011, 619-627, vol. 27, No. 5, Elsevier, US.

* cited by examiner

*Primary Examiner* — Thane Underdahl
(74) *Attorney, Agent, or Firm* — Brigitte C. Phan; Ted A. Chan

(57) ABSTRACT

Methods for treating or alleviating symptoms associated with femoroacetabular impingement (FAI) by local administration of a clostridial derivative, such as a botulinum toxin, to the hip capsule and surrounding muscle.

20 Claims, 1 Drawing Sheet

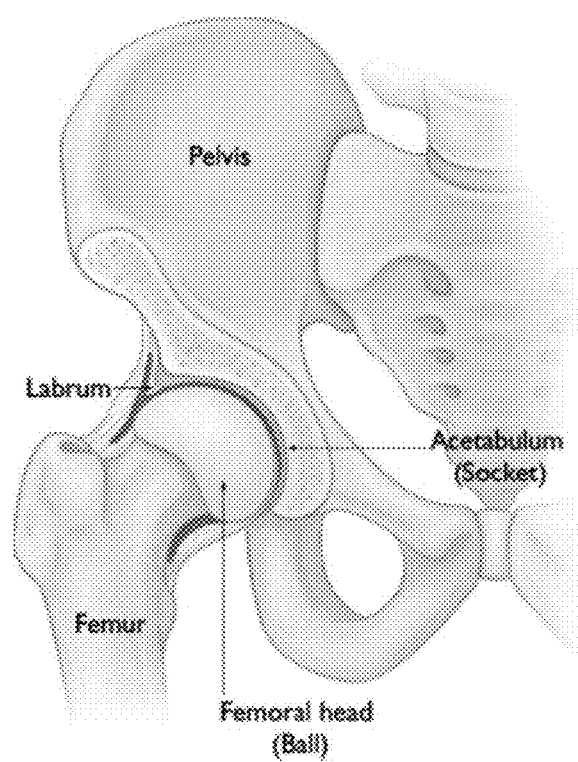

METHODS FOR TREATMENT OF HIP AND GROIN PAIN ASSOCIATED WITH FEMOROACETABULAR IMPINGEMENT (FAI)

CROSS REFERENCE TO RELATED APPLICATIONS

This application claims the benefit of U.S. Provisional Application Ser. No. 61/815,902, filed Apr. 25, 2013 incorporated herein entirely by reference.

FIELD

The present disclosure relates to methods for treatment of hip and groin pain. In particular, the present disclosure relates to the treatment of Femoroacetabular Impingement (FAI) syndrome using neurotoxins.

BACKGROUND

Hip and groin pain has for many years been a difficult diagnostic challenge. In the past decade there has been increased focus on femoroacetabular impingement (FAI) as a cause. FAI is now considered by many as a primary cause of hip joint degeneration.

The hip joint is a "ball-and-socket" joint located where the femur (thigh bone) meets the pelvic bone (FIG. 1). The upper segment ("femoral head") of the femur is a round ball that fits inside the cavity of the pelvic bone that forms the socket, also known as the acetabulum. The femoral head is held in the acetabulum by a network of ligaments that form a capsule around the joint. This capsule of ligaments contains synovial fluid which acts as a lubricant. A smooth cartilage covers the femoral head and the acetabulum and provides a smooth, low friction surface that allows the bones to glide easily across each other. The acetabulum is lined with a fibrocartilage termed labrum which forms a gasket around the acetabulum ensuring a snug fit of the femoral head within the acetabulum.

In FAI, bone overgrowth develops around the femoral head and/or along the acetabulum, causing the bones to hit against each other, rather than to move smoothly. Over time, this repetitive impact can result in the tearing of the labrum and breakdown of the cartilage (osteoarthritis).

There are three main types of FAI: (1) Cam impingement, (2) Pincer impingement, and (3) a combination of Cam and Pincer impingement. In Cam impingement, excess bone forms around the femoral head, such that the femoral head is not round and cannot rotate smoothly inside the acetabulum. In Pincer impingement, excess bone extends out of the acetabulum, which may damage the labrum, or the acetabulum is angled in such a way that abnormal impact occurs between the femoral head and the acetabulum. Cam impingement typically affects young males while Pincer impingement is more common among older females. Morphologic abnormalities of the bones may predispose a patient to FAI. Sporting activities, such as the ones that involve a repetitive axial load through the hip or frequent pivoting movements resulting in torsional forces, may contribute to the development of FAI lesions, although the exact mechanism by which this happens is unclear.

As a result of abnormal impact between the femoral head and the acetabulum, the femoral head does not have its full range of motion within the acetabulum. Symptoms of FAI include pain in the groin and hip area, restricted range of hip joint motion, progressive muscle weakness and reduced flexibility.

Current therapies for FAI include anti-inflammatory medications and activity modifications, steroid injections, and surgical options. Anti-inflammatory medications, including non-steroidal anti-inflammatory drugs (NSAIDS) such as aspirin and ibuprofen; and opioids, and activity modification may provide short term relief but do not address the underlying problem. Steroid injections have long term side effects, including cartilage break down. Surgical options, such as open, arthroscopic and combined techniques, are intensive, and involve long recovery period.

Thus, there is a need for alternative treatment methods that treat or alleviate symptoms associated with FAI.

SUMMARY

Aspects of the present disclosure provide a method for effectively treating and/or alleviation FAI associated symptoms. In some embodiments, the present method alleviates the pain, discomfort, inflammation and limited ranges of mobility associated with FAI. In one aspect, the present method comprises locally administering a clostridial derivative to a patient suffering from FAI. In some embodiments, the clostridial derivative is a native or recombinant neurotoxin, a recombinant modified toxin, fragments thereof, a Targeted vesicular Exocytosis Modulator (TEM), or combinations thereof. In one embodiment, the present method comprises locally administering a clostridial derivative into the hip capsule of the patient.

In some embodiments, the present method comprises locally administering a clostridial derivative into the hip capsule and/or surrounding muscles of the patient.

In one embodiment, the present disclosure provides a method for alleviating at least one symptom associated with femoroacetabular impingement in a patient in need thereof, the method comprising locally administering a therapeutically effective amount of clostridial derivative to a hip capsule at a location between the acetabulum and femoral head of the patient, thereby alleviating the at least one symptom. In one embodiment, the clostridial derivative is administered intraarticularly. In another embodiment, the clostridial derivative is administered extraarticularly.

In some embodiments, the present method comprises locally administering a clostridial derivative into the hip capsule and/or surrounding muscles of the patient. In some embodiments, the present method comprises administering a clostridial derivative into the hip capsule and the iliopsoas muscle of the patient.

In some aspects, the present method comprises locally administering a clostridial derivative into the hip capsule and/or surrounding muscles of the patient and administering anti-inflammatory medicines to the patient.

In some embodiments, the present method comprises locally administering a clostridial derivative into the hip capsule and/or surrounding muscles of the patient and locally administering viscosupplements to the hip capsule of the patient.

In some embodiments, the present method comprises locally administering a clostridial derivative into the hip capsule and/or surrounding muscles of the patient prior to or in conjunction with administering physical therapy to the patient.

In another aspect, the present disclosure provides a method for post operatively alleviating the pain, discomfort and inflammation in a patient who have had prior FAI corrective surgery, the method comprising locally administering a clostridial derivative into the hip capsule and/or surrounding muscles of the patient. In alternative embodiments, the method further comprises administering anti-inflammatory medicines, viscosupplements and/or physical therapy to the patient.

In another aspect, the present disclosure provides a method for delaying surgical treatment for a patient suffering from femoroacetabular impingement, the method comprises administering a therapeutically effective amount of a clostridial derivative to a capsule of ligaments located between the acetabulum and femoral head of the patient between the acetabulum and femoral head of the patient.

In another aspect, by alleviating FAI associated symptoms in a patient suffering from FAI, the present method provides functional improvement and thus improves the quality of life for the patient.

BRIEF DESCRIPTION OF THE FIGURES

The following drawings are presented to illustrate aspects and features of embodiments of the present invention.

FIG. 1 shows the anatomy of a hip joint.

DESCRIPTION

In certain embodiments, the dose of a clostridial derivative, such as a botulinum toxin, used according to embodiments of the present invention is less than the amount of botulinum toxin that would be used to paralyze a muscle, because an intent of a method according to embodiments of the present disclosure is not to paralyze a muscle but to reduce a pain sensory output from sensory neurons innervating the hip joint or surrounding muscle and/or to relax the surrounding overactive muscles and ligaments.

Botulinum neurotoxins (BoNTs) such as, for example, BoNT/A, BoNT/B, etc., act on the nervous system by blocking the release of neurosecretory substances such as neurotransmitters. The action of BoNT is initiated by its binding to a receptor molecule on the cell surface, then the toxin-receptor complex undergoes endocytosis. Once inside the cell, BoNT cleaves exocytotic specific proteins responsible for neurotransmitter docking and release from the cell known as the SNARE proteins (soluble N-ethylmaleimide-sensitive factor attachment protein receptor). The resulting transient chemodenervation has been utilized medically to block motor neurotransmission at the neuromuscular junction leading to a variety of therapeutic applications.

The following definitions apply herein:

"About" or "approximately" as used herein means within an acceptable error range for the particular value as determined by one of ordinary skill in the art, which will depend in part on how the value is measured or determined, (i.e., the limitations of the measurement system). For example, "about" can mean within 1 or more than 1 standard deviations, per practice in the art. Where particular values are described in the application and claims, unless otherwise stated, the term "about" means within an acceptable error range for the particular value.

"Administration", or "to administer" means the step of giving (i.e. administering) a botulinum toxin to a subject, or alternatively a subject receiving a pharmaceutical composition. The present method can be performed via administration routes including intramuscular, non-intramuscular, intraarticular, extraarticular, intradermal, subcutaneous administration, intrathecal administration, intraperitoneal administration, implantation (for example, of a slow-release device such as polymeric implant or miniosmotic pump), or combinations thereof.

"Alleviating" means a reduction in the occurrence of a pain, of FAI associated pain or of other FAI associated symptoms. Thus, alleviating includes some reduction, significant reduction, near total reduction, and total reduction. An alleviating effect may not appear clinically for between 1 to 7 days after administration of a Botulinum toxin to a patient or sometime thereafter.

"Botulinum toxin" means a neurotoxin produced by *Clostridium botulinum*, as well as a botulinum toxin (or the light chain or the heavy chain thereof) made recombinantly by a non-Clostridial species. The term "botulinum toxin", as used herein, encompasses the botulinum toxin serotypes A, B, C, D, E, F and G, and their subtypes and any other types of subtypes thereof, or any re-engineered proteins, analogs, derivatives, homologs, parts, sub-parts, variants, or versions, in each case, of any of the foregoing. "Botulinum toxin", as used herein, also encompasses a "modified botulinum toxin". Further "botulinum toxin" as used herein also encompasses a botulinum toxin complex, (for example, the 300, 600 and 900 kDa complexes), as well as the neurotoxic component of the botulinum toxin (150 kDa) that is unassociated with the complex proteins.

"Clostridial derivative" refers to a molecule which contains any part of a clostridial toxin. As used herein, the term "clostridial derivative" encompasses native or recombinant neurotoxins, recombinant modified toxins, fragments thereof, a Targeted vesicular Exocytosis Modulator (TEM), or combinations thereof.

"Clostridial toxin" refers to any toxin produced by a Clostridial toxin strain that can execute the overall cellular mechanism whereby a Clostridial toxin intoxicates a cell and encompasses the binding of a Clostridial toxin to a low or high affinity Clostridial toxin receptor, the internalization of the toxin/receptor complex, the translocation of the Clostridial toxin light chain into the cytoplasm and the enzymatic modification of a Clostridial toxin substrate.

"Effective amount" as applied to the biologically active ingredient means that amount of the ingredient which is generally sufficient to induce a desired change in the subject. For example, where the desired effect is a reduction in FAI associated symptoms, an effective amount of the ingredient is that amount which causes at least a substantial reduction of the FAI associated symptoms, and without resulting in significant toxicity.

"Implant" means a controlled release (e.g., pulsatile or continuous) composition or drug delivery system. The implant can be, for example, injected, inserted or implanted into a human body.

"Intraarticular injection" refers to an injection directly into a joint.

"Extraarticular injection" refers to an injection outside of a joint space.

"Local administration" means administration of a pharmaceutical agent to or to the vicinity of a muscle or a subdermal location in a patient by a non-systemic route. Thus, local administration excludes systemic routes of administration, such as intravenous or oral administration.

"Peripheral administration" means administration to a location away from a symptomatic location, as opposed to a local administration.

"TEMs", abbreviated for Targeted Exocytosis Modulators are retargeted endopeptidases that direct the catalytic activity of the light chain to specific types of neuronal cells or to target cells that were not affected by botulinum toxins expanding the beneficial clinical effect of inhibition of exocytosis in several human diseases.

"Treating" or "treatment" means to alleviate (or to eliminate) at least one symptom (such as, for example, hip and groin pain), either temporarily or permanently.

"Therapeutically effective amount" refers to an amount sufficient to achieve a desired therapeutic effect.

Aspects of the present disclosure provide in part a method for treating and/or alleviating at least one symptom associated with FAI. In some embodiment, the present method comprises locally administering a therapeutically effective amount of a clostridial derivative to a hip capsule at a location between the acetabulum and the femoral head of the patient, thereby alleviating the at least one symptom. In some embodiments, the clostridial derivative is administered by intraarticular injections. In other embodiments, the clostridial derivative is administered by extraarticular injections. In some embodiments, the present method further comprises administering the clostridial derivative into extraarticular tissues, such as the lumbosacral spine, iliopsoas, adductors, abdominal aponeurosis, iliotibial band, bursae, or gluteal muscles. In some embodiments, the clostridial derivative is administered to the extraarticular tissues by intramuscular injections. In alternative embodiments, the administration to the extraarticular tissues is by non-intramuscular injections.

In some embodiments, the present method comprises administering the clostridial derivative to the hip capsule and to the thigh muscles. In one embodiment, the present method comprises administering the clostridial derivative to the hip capsule and the upper thigh muscles, including but not limited to the long adductor muscle, the great adductor muscle, the iliopsoas muscle, and the tensor muscle of the fascia lata. In one embodiment, the present method comprises locally administering a clostridial derivative into the hip capsule and one of the long adductor muscle, the great adductor muscle, the iliopsoas muscle, the tensor muscle of the fascia lata, or combinations thereof. In one particular embodiment, the present method comprises locally administering a clostridial derivative into the hip capsule and the iliopsoas muscle.

In some embodiments, the administration to the hip capsule is radiologic guided. In one embodiment, the administration is ultrasound guided. In other embodiments, the administration is fluoroscopy (live X-ray) guided using X ray dyes. In some embodiments, the administration is guided with an electromyographic guide.

The hip joint capsule is innervated by sensory articular branches from the femoral nerves, sciatic nerves, superior gluteal nerves. In some embodiments, the clostridial derivative is administered specifically to sensory articular nerves, including femoral nerves, sciatic nerves, superior gluteal nerves, or combinations thereof. In some embodiments, the clostridial derivative may be administered around the nerve endings of the femoral nerves, sciatic nerves, superior gluteal nerves, or combinations thereof. In some embodiments, the clostridial derivative may be administered by injections, and radiologic guided. In some embodiments, the clostridial derivative is administered the articular nerves and to the upper thigh muscles, including but not limited to the long adductor muscle, the great adductor muscle, the iliopsoas muscle, and the tensor muscle of the fascia lata.

In some embodiments, the clostridial derivative includes a native, recombinant clostridial toxin, recombinant modified toxin, fragments thereof, TEMs, or combinations thereof. In some embodiments, the clostridial derivative is a botulinum toxin. In some embodiments, the botulinum toxin can be a botulinum toxin type A, type B, type $C_1$, type D, type E, type F, or type G, or any combination thereof. The botulinum neurotoxin can be a recombinantly made botulinum neurotoxins, such as botulinum toxins produced by $E.$ $coli$. In alternative embodiments, the clostridial derivative is a TEM.

In some embodiments, the botulinum neurotoxin can be a modified neurotoxin, that is a botulinum neurotoxin which has at least one of its amino acids deleted, modified or replaced, as compared to a native toxin, or the modified botulinum neurotoxin can be a recombinant produced botulinum neurotoxin or a derivative or fragment thereof. In certain embodiments, the modified toxin has an altered cell targeting capability for a neuronal or non-neuronal cell of interest. This altered capability is achieved by replacing the naturally-occurring targeting domain of a botulinum toxin with a targeting domain showing a selective binding activity for a non-botulinum toxin receptor present in a non-botulinum toxin target cell. Such modifications to a targeting domain result in a modified toxin that is able to selectively bind to a non-botulinum toxin receptor (target receptor) present on a non-botulinum toxin target cell (re-targeted). A modified botulinum toxin with a targeting activity for a non-botulinum toxin target cell can bind to a receptor present on the non-botulinum toxin target cell, translocate into the cytoplasm, and exert its proteolytic effect on the SNARE complex of the target cell. In essence, a botulinum toxin light chain comprising an enzymatic domain is intracellularly delivered to any desired cell by selecting the appropriate targeting domain.

The clostridial derivative, such as a botulinum toxin, for use according to the present invention can be stored in lyophilized, vacuum dried form in containers under vacuum pressure or as stable liquids. Prior to lyophilization the botulinum toxin can be combined with pharmaceutically acceptable excipients, stabilizers and/or carriers, such as, for example, albumin, or the like. In embodiments containing albumin, the albumin can be, for example, human serum albumin, or the like. The lyophilized material can be reconstituted with a suitable liquid such as, for example, saline, water, or the like to create a solution or composition containing the botulinum toxin to be administered to the patient.

In some embodiments, the clostridial derivative is provided in a controlled release system comprising a polymeric matrix encapsulating the clostridial derivative, wherein fractional amount of the clostridial derivative is released from the polymeric matrix over a prolonged period of time in a controlled manner. Controlled release neurotoxin systems have been disclosed for example in U.S. Pat. Nos. 6,585, 993; 6,585,993; 6,306,423 and 6,312,708, each of which is hereby incorporated by reference in its entirety.

The therapeutically effective amount of the clostridial derivative, for example a botulinum toxin, administered according to the present method can vary according to the potency of the toxin and particular characteristics of the pain being treated, including its severity and other various patient variables including size, weight, age, and responsiveness to therapy. The potency of the toxin is expressed as a multiple of the $LD_{50}$ value for the mouse, one unit (U) of toxin being defined as being the equivalent amount of toxin that kills 50% of a group of 18 to 20 female Swiss-Webster mice, weighing about 20 grams each.

The therapeutically effective amount of the botulinum toxin, in the present method can vary according to the potency of a particular botulinum toxin, as commercially available Botulinum toxin formulations do not have equivalent potency units. For example, one unit of BOTOX®

(onabotulinumtoxinA), a botulinum toxin type A available from Allergan, Inc., has a potency unit that is approximately equal to 3 to 5 units of DYSPORT® (abobotulinumtoxinA), also a botulinum toxin type A available from Ipsen Pharmaceuticals. MYOBLOC®, a botulinum toxin type B available from Elan, has a much lower potency unit relative to BOTOX®. In some embodiments, the botulinum neurotoxin can be a pure toxin, devoid of complexing proteins, such as XEOMIN® (incobotulinumtoxinA). One unit of IncobotulinumtoxinA has a potency approximately equivalent to one unit of onabotulinumtoxinA. Thus, the quantity of toxin administered and the frequency of its administration will be at the discretion of the physician responsible for the treatment and will be commensurate with questions of safety and the effects produced by a particular toxin formulation.

The dosages used in human therapeutic applications are roughly proportional to the mass of the tissue being injected. Typically, the dose administered to the patient may be up from about 0.01 to about 1,000 units; for example, up to about 500 units, and preferably in the range from about 80 to about 460 units per patient per treatment, although smaller of larger doses may be administered in appropriate circumstances such as about 50 units for the relief of FAI associated symptoms.

In some embodiments, the present method comprises administering 10-500 units of a botulinum toxin type A, such as BOTOX®, intraarticularly into the hip capsule. In some embodiments, the present method comprises administering 25-100 units of BOTOX® intraarticularly into a single hip capsule. In one specific embodiment, the present method comprises administering 10-500 units of BOTOX® intraarticularly into the hip capsule and 10-500 units into one of the long adductor muscle, the great adductor muscle, the iliopsoas muscle, the tensor muscle of the fascia lata, or combinations thereof. In one specific embodiment, 25-100 units of BOTOX® is injected intraarticularly into the hip capsule and 10-50 units into one of the long adductor muscle, the great adductor muscle, the iliopsoas muscle, the tensor muscle of the fascia lata, or combinations thereof. In alternative embodiments, the present method comprises administering 40-1200 units of DYSPORT® intraarticularly into the hip capsule and 40-2000 units of DYSPORT® into one of the long adductor muscle, the great adductor muscle, the iliopsoas muscle, the tensor muscle of the fascia lata, or combinations thereof.

The treatment effects of the botulinum toxin can persist for between about 1 month and 5 years. Administration can be repeated as necessary. As a general guideline, botulinum toxin type A administered into or near muscle tissue has been observed to produce flaccid paralysis at target site muscles for up to about 3 to 6 months. However, increased efficacy of the treatment using botulinum toxin type A is expected to happen when the toxin is administered according to the disclosed method at about 3 month intervals.

In some embodiments, the present method further comprises administering viscosupplements to the hip capsule of the patient. Viscosupplements suitable for the present method include hyaluronate formulations, such as ADANT®, SYNOCROM® or SYNVISC®. The viscosupplements can be administered concurrently, prior to and/or subsequent to the administration of the clostridial derivative. Viscosupplements administration to restore elastoviscosity of the joint (dosage, frequency, mode) can be carried out as well known to one of ordinary skill in the art.

In alternative embodiments, the present method further comprises administering anti-inflammatory medications to the patient. In one embodiment, the present method comprises further administering non-steroidal anti-inflammatory drugs (NSAIDS) to the patient such as aspirin and ibuprofen; and opioids, such as morphine. The NSAIDS administration can be provided concurrently, prior to and/or subsequent to the administration of the botulinum toxin. NSAIDS administration for pain relief (dosage, frequency, mode) can be carried out as well known to one of ordinary skill in the art. In alternative embodiments, the present method further comprises administering steroids to the patients. In one embodiment, the steroids are administered are locally. In one specific embodiment, the steroids administration is by intraarticular injections. In alternative embodiments, the steroids administration is by extraarticular injections.

Aspects of the present disclosure provide a method for enhancing the effectiveness of physical therapy for a patient suffering from FAI, the method comprises locally administering a therapeutically effective amount of a clostridial derivative into the hip capsule and/or surrounding muscles of the patient prior to and/or in conjunction with administration of physical therapy to the patient. In one embodiment, the clostridial derivative is administered prior to administration of physical therapy to the patient. In an alternative embodiment, the clostridial derivative is administered during administration of physical therapy to the patient. The present method enhances the effectiveness of physical therapy by multiple routes, such as for example relaxing the muscles and expanding the joint capsule, thus facilitating the patient's movements and flexibility, muscle strengthening, and/or reducing the pain, expanding the range of motion, thus allowing the patient's to respond more effectively to the physical therapy.

In another aspect, the present disclosure provides a method for post operatively alleviating the pain, discomfort and inflammation in a patient who have had prior FAI corrective surgery, the method comprising locally administering a therapeutically effective amount of a clostridial derivative into the hip capsule and/or surrounding muscles of the patient. In alternative embodiments, the method further comprises administering anti-inflammatory medicines, viscosupplements and/or physical therapy to the patient.

In another aspect, the present disclosure provides a method for delaying surgical treatments for treating FAI, the method comprising locally administering a therapeutically effective amount of a clostridial derivative into the hip capsule and/or surrounding muscles of the patient. In alternative embodiments, the method further comprises administering anti-inflammatory medicines, e.g. steroid injections, viscosupplements and/or physical therapy to the patient.

A method within the scope of the present disclosure can provide improved patient function. "Improved patient function" can be defined as an improvement measured by factors such as a reduced pain, increased ambulation, healthier attitude, more varied lifestyle and/or healing permitted by normal muscle tone and function. Improved patient function is may be measured with an improved quality of life (QOL) or Health-Related Quality of Life (HRQL). Scores obtained can be compared to published values available for various general and patient populations.

The following non-limiting examples provide those of ordinary skill in the art with specific preferred methods to treat FAI-associated symptoms within the scope of the present disclosure, and it is not intended to limit the scope of the invention. In the following examples various modes of non-systemic administration of a botulinum neurotoxin can be carried out. For example, by intramuscular injection, non-intramuscular injection, intraarticular injection, extraarticular injection, subcutaneous injection or by implantation of a controlled release implant.

EXAMPLES

The following non-limiting examples provide those of ordinary skill in the art with specific preferred methods to treat conditions within the scope of embodiments of the present invention and are not intended to limit the scope of the invention.

Example 1

Botulinum Toxin Type A Therapy for FAI Associated Symptoms

A 30-year-old male plays adult soccer and is a part-time mechanic. He trains or plays at least four times per week. He complains of a six-month history of right groin pain, of insidious onset, precipitated by running and twisting at speed in training and high flexing when kicking and often lasting for 12-24 hours after a vigorous match or training session. The pain is occasionally associated with clicking within his hip. The pain is localized deep inside his hip and he grips his trochanter as he tries to describe its location. Usually pain is temporarily relieved by simple analgesics, stretching the hip capsule and rest. He has visited a local physical therapist for two courses of physical therapy and completely abstained from all sport for six weeks and found the pain disappeared but on return to his training symptoms return as before. MRI scanning reveals a slight labral tear and anterosuperior impingement lesion on the femoral neck.

The patient is treated with 100 Units of Botulinum toxin type A by direct intraarticular injection into the hip capsule. After 3 days, the symptoms started to improve with significant improvement observed at week 12.

Example 2

The treatment described in Example 1 is repeated, and followed by viscosupplements administration. After 2-3 days, the symptoms the symptoms started to improve with significant improvement observed at week 12.

Example 3

The treatment described in Example 1 is repeated, and following by administration of physical therapy. After 5 days, the symptoms started to improve with significant improvement observed at week 12.

Example 4

The patient of Example 1 is treated by injection of 100 units of Botulinum toxin type A by direct injection into the hip capsule and 50 units of Botulinum toxin type A into the iliopsoas muscle. After 3 days, the symptoms started to improve with significant improvement observed at week 12.

Example 5

An active 34-year-old female who plays women ice hockey and is an avid weekend cyclist presents with three months of right anterior hip pain. The pain lies deep in the groin and she localizes it by cupping her hand over the greater trochanter. Pain is precipitated by skating with an extended stride and cycling great distances. Often it is after a game when she is most limited. She has had to miss the end of the hockey season and give up her plans to cycle in a 65 mile charity drive. Her physical therapist has used a variety of techniques including manipulation and stretches which fail to resolve the pain. She takes simple anti-inflammatory medication to ease the pain. More recently she has found the 20-minute walk to work a struggle. An x-ray of her pelvis is reported as showing mild acetabular dysplasia but no significant abnormality. An MRI scan shows a labral tear, a paralabral cyst and early chondral damage in the anterosuperior acetabulum.

The patient is treated with 200 units of a botulinum toxin A divided into several areas, including the hip capsule, the long adductor muscle, the great adductor muscle and the iliopsoas muscle. Moderate relief of symptoms associated with FAI occurs in about 5 days with significant improvement in three months.

Example 6

The treatment described in Example 5 is repeated, and followed by steroid injections. Moderate relief of symptoms associated with FAI occurs in about 5 days with significant improvement in three months.

Example 7

The treatment described in Example 5 is repeated, and following by administration of physical therapy. Moderate relief of symptoms associated with FAI occurs in about 5 days with significant improvement in three months.

Many alterations and modifications may be made by those having ordinary skill in the art, without departing from the spirit and scope of the disclosure. Therefore, it must be understood that the described embodiments have been set forth only for the purposes of examples, and that the embodiments should not be taken as limiting the scope of the following claims. The following claims are, therefore, to be read to include not only the combination of elements which are literally set forth, but all equivalent elements for performing substantially the same function in substantially the same way to obtain substantially the same result. The claims are thus to be understood to include those that have been described above, those that are conceptually equivalent, and those that incorporate the ideas of the disclosure.

I claim:

1. A method for alleviating at least one symptom associated with femoroacetabular impingement in a patient suffering therefrom, the method comprising locally administering a therapeutically effective amount of a botulinum toxin to a hip capsule located between the acetabulum and the femoral head of the patient, thereby alleviating the at least one symptom.

2. The method of claim 1, further comprising administering a therapeutically effective amount of the botulinum toxin to an upper thigh muscle of the patient.

3. The method of claim 2, wherein the upper thigh muscle is selected from the group consisting of the long adductor muscle, the great adductor muscle, the iliopsoas and tensor muscle of the fascia lata.

4. The method of claim 3, wherein the upper thigh muscle is the iliopsoas muscle.

5. The method of claim 1, further comprising administering viscosupplements to the hip capsule of the patient.

6. The method of claim 1, further comprising administering anti-inflammatory medications to the patient.

7. The method of claim 1, further comprising administering steroids to the patient.

8. The method of claim 1, further comprising administering physical therapy to the patient.

9. The method of claim 1 wherein the botulinum toxin is selected from the group consisting of botulinum toxin types A, B, C, D, E, F and G.

10. The method of claim 9, wherein the botulinum neurotoxin is type A.

11. A method for delaying surgical treatment for a patient suffering from femoroacetabular impingement, the method comprises administering a therapeutically effective amount of a botulinum toxin to an area between the acetabulum and femoral head of the patient, thereby alleviating at least one symptom associated with femoroacetabular impingement.

12. The method of claim 11, further comprising administering a therapeutically effective amount of the botulinum toxin to an upper thigh muscle of the patient.

13. The method of claim 12, wherein the upper thigh muscle is selected from the group consisting of the long adductor muscle, the great adductor muscle, the iliopsoas and tensor muscle of the fascia lata.

14. The method of claim 13, wherein the upper thigh muscle is the iliopsoas muscle.

15. The method of claim 11, further comprising administering viscosupplements to the hip capsule of the patient.

16. The method of claim 11, further comprising administering anti-inflammatory medications to the patient.

17. The method of claim 11, further comprising administering steroids to the patient.

18. The method of claim 11, further comprising administering physical therapy to the patient.

19. The method of claim 11, wherein the botulinum toxin is selected from the group consisting of botulinum toxin types A, B, C, D, E, F and G.

20. The method of claim 19, wherein the botulinum neurotoxin is type A.

* * * * *